(12) United States Patent
Wu

(10) Patent No.: US 7,780,349 B2
(45) Date of Patent: Aug. 24, 2010

(54) APPARATUS AND METHOD FOR ROBOTIC RADIOSURGERY BEAM GEOMETRY QUALITY ASSURANCE

(75) Inventor: Xiaodong Wu, Miami, FL (US)

(73) Assignee: James G. Schwade, Miami, FL (US), part interest ( * ) Notice: Subject to any disclaimer, the term of this patent is extended or adjusted under 35 U.S.C. 154(b) by 35 days.

(21) Appl. No.: 12/006,629

(22) Filed: Jan. 3, 2008

(65) Prior Publication Data

US 2008/0170671 A1 Jul. 17, 2008

Related U.S. Application Data

(60) Provisional application No. 60/878,247, filed on Jan. 3, 2007.

(51) Int. Cl.
*A61B 6/08* (2006.01)
*A61N 5/10* (2006.01)

(52) U.S. Cl. .................. 378/205; 378/65; 378/163

(58) Field of Classification Search ............... 378/65, 378/163, 164, 205
See application file for complete search history.

(56) References Cited

U.S. PATENT DOCUMENTS

| 5,283,808 | A | * | 2/1994 | Cramer et al. ............ 378/206 |
| 5,494,034 | A | | 2/1996 | Schlondorff |
| 5,517,990 | A | | 5/1996 | Kalfas |
| 5,755,725 | A | | 5/1998 | Druais |
| 5,954,647 | A | | 9/1999 | Bova et al. |
| 5,987,960 | A | | 11/1999 | Messner et al. |
| 6,026,315 | A | | 2/2000 | Lenz et al. |
| 6,351,659 | B1 | | 2/2002 | Vilsmeier |
| 6,377,839 | B1 | | 4/2002 | Kalfas et al. |
| 6,379,041 | B1 | * | 4/2002 | Schuetz et al. ............ 378/205 |
| 6,490,475 | B1 | | 12/2002 | Seeley et al. |
| 6,497,134 | B1 | | 12/2002 | Faul et al. |
| 6,614,036 | B1 | | 9/2003 | Reinstein et al. |
| 6,662,036 | B2 | * | 12/2003 | Cosman .................... 600/411 |
| 6,782,287 | B2 | | 8/2004 | Grzesczuk et al. |
| 7,043,961 | B2 | | 5/2006 | Pandey et al. |

(Continued)

OTHER PUBLICATIONS

Wu X. et al, The Cyberknife Physics QA: An Institutional Perspective. Cyberknife 5th Users' Meeting, Carlsbad, California, Jan. 25-27, 2006.

*Primary Examiner*—Edward J Glick
*Assistant Examiner*—Thomas R Artman
(74) *Attorney, Agent, or Firm*—Pinkert Law Firm, P.A.; Steven Pinkert, Esq

(57) ABSTRACT

A method and apparatus for quality assurance of beam geometry of robotic radiosurgery systems. The apparatus comprises two or more radio-opaque markers set at a fixed distance from each other and contained in a housing, which is assembled to a collimator fixture for attachment to the collimator interface of the LINAC of a robotic radiosurgery system. A treatment plan is generated to position the LINAC to a series of pre-defined radiation beam orientations, then a simulation of the treatment is carried out, and radiographic images are taken at each LINAC position. The coordinates of the radio-opaque markers obtained from the images are used to determine beam orientation by calculating their directional cosines, the beam off-axis error and the deviation of the radiation source to iso-center distance (SAD). The imaging system is independently calibrated and the quantitative beam geometric information is used to adjust beam geometry for quality assurance.

5 Claims, 4 Drawing Sheets

U.S. PATENT DOCUMENTS

| | | | |
|---|---|---|---|
| 7,125,165 B2 * | 10/2006 | Lutjens et al. | 378/205 |
| 7,139,601 B2 | 11/2006 | Bucholz et al. | |
| 7,349,730 B2 * | 3/2008 | Ein-Gal | 600/427 |
| 7,356,120 B2 * | 4/2008 | Main et al. | 378/65 |
| 7,505,559 B2 * | 3/2009 | Kuduvalli | 378/65 |
| 2002/0181660 A1 | 12/2002 | Reinstein et al. | |
| 2006/0045238 A1 | 3/2006 | Nguyen | |
| 2006/0079764 A1 | 4/2006 | Wright et al. | |
| 2006/0093089 A1 | 5/2006 | Vertatschitsch et al. | |
| 2006/0100509 A1 | 5/2006 | Wright et al. | |
| 2007/0071176 A1 | 3/2007 | Main et al. | |
| 2007/0127622 A1 | 6/2007 | Main et al. | |

* cited by examiner

US 7,780,349 B2

APPARATUS AND METHOD FOR ROBOTIC RADIOSURGERY BEAM GEOMETRY QUALITY ASSURANCE

CROSS-REFERENCE TO RELATED APPLICATIONS

This application claims the benefit of U.S. Provisional Application No. 60/878,247, filed Jan. 3, 2007. The entire disclosure of this prior application is hereby incorporated by reference.

STATEMENT REGARDING FEDERALLY SPONSORED RESEARCH OR DEVELOPMENT

This invention has been created without the sponsorship or funding of any federally sponsored research or development program.

FIELD OF THE INVENTION

The present invention relates generally to the field of quality assurance (QA) of the beam geometry of robotic radiosurgery systems with image-guided radiation treatment delivery systems delivering beams of radiation to a target from multiple predefined beam directions. The QA of beam geometry is very important for obtaining optimum and precise clinical results from robotic radiosurgery treatments.

BACKGROUND OF THE INVENTION

Robotic radiosurgery systems, such as CyberKnife™, use a high-precision robotic manipulator, with an image-guided system delivering beams of radiation to the target from multiple predefined beam directions. Since the total clinical precision of robotic radiosurgery treatment ultimately depends on the accuracy and reproducibility of each beam direction, the quality assurance (QA) of beam geometry is of paramount importance. The current method (old) of verifying the predefined beam geometry involves directing the internal laser onto the crystal of an iso-post and adjusting beam position based on the signal generated from the crystal, until the maximum signal is reached. Since the crystal is affixed at the system's iso-center, the old procedure is designed to ascertain the alignment of the beam central axis with the system's iso-center. However, there are several drawbacks to this method: first, the precise laser alignment must be achieved, which is a difficult task, second, the old method does not yield beam angular information, third, it does not yield information about the distance between the radiation source and the system's iso-center (SAD), and fourth, the beam adjustment is a random search process which makes the procedure time-consuming.

This invention was conceived to access full beam geometric parameters by radiographic visualization of the beam central axis. The procedure designed for using this device reveals the inaccuracy of the imaging system and the error in robotic precision. Once the imaging system is independently calibrated, the new apparatus and method provides information to adjust the beam geometry to the optimum specification.

SUMMARY OF THE INVENTION

This present invention provides a new method and apparatus for use with robotic radiosurgery systems, such as Cyberknife™, to access full beam geometric parameters. It is the object of this invention to allow clinicians to gain a radiographic visualization of the beam central axis and enable them to detect the inaccuracy of the imaging system and error in robotic precision. The imaging system is independently calibrated and the information obtained is used to adjust the beam geometry to the optimum specification.

BRIEF DESCRIPTION OF THE DRAWINGS

In describing the invention, reference will at times be made to the accompanying drawings in which:

FIG. 2A-1 is a superimposed view of the assembled component of the invention;

DETAILED DESCRIPTION

Before the subject invention is described further, it is to be understood that the invention is not limited to the particular embodiments of the invention described below, as variations of the particular embodiments may be made and still fall within the scope of the invention. It is also to be understood that the terminology employed is for the purpose of describing particular embodiments, and is not intended to be limiting.

The details of one or more embodiments of the invention are set forth in the accompanying drawings and the description below. Other features, objects, and advantages of the invention will be apparent from the description and drawings, and from the claims. In the following description, numerous specific details are set forth to provide a thorough understanding of the embodiments. One skilled in the art to which this invention belongs will recognize, however, that the techniques described can be practiced without one or more of the specific details, or with other methods, components, materials, etc. In other instances, well known structures, materials or operations are not shown or described in detail to avoid obscuring certain aspects.

In this specification, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Figure 1:
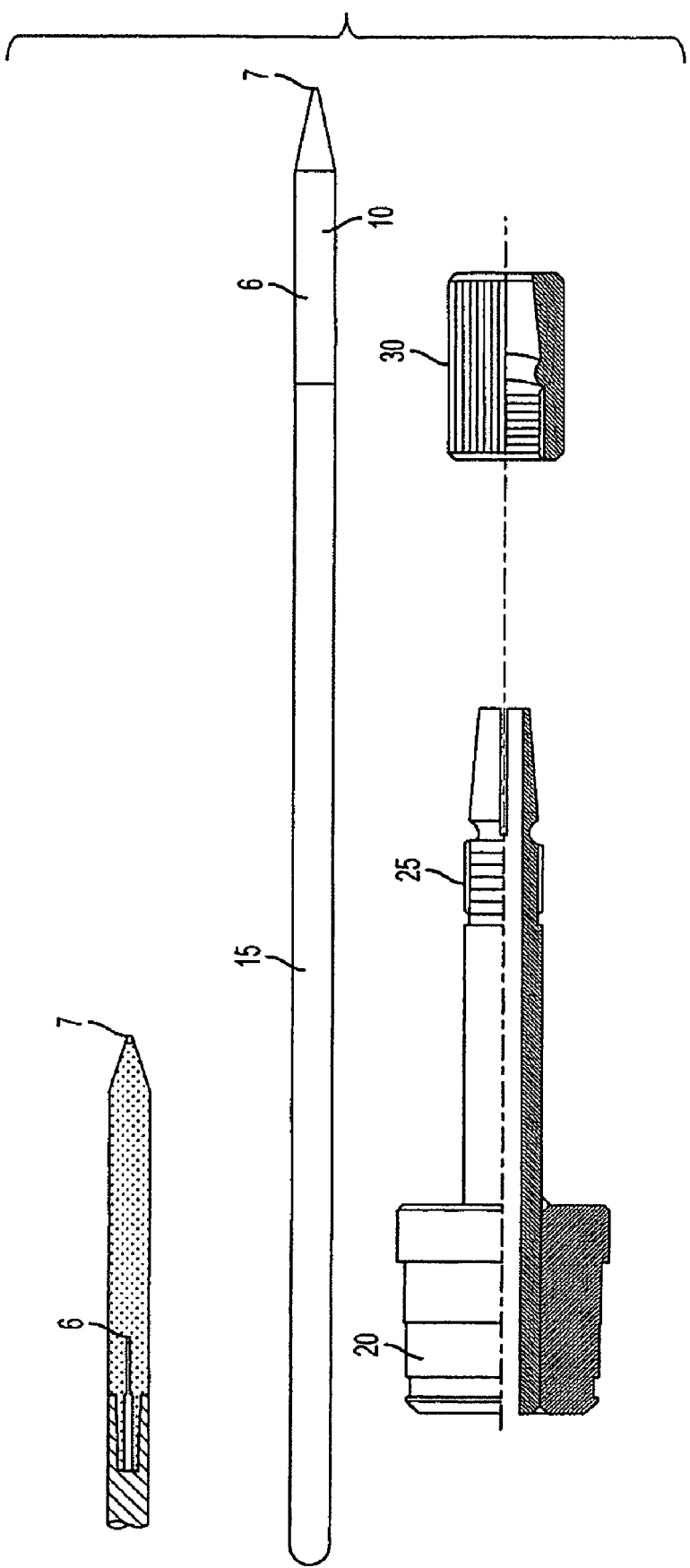
FIG. 1 is a cross sectional view of the components comprising the apparatus of the new invention.

FIG. 1 is a diagram of the apparatus designed to access full beam geometry in image guided robotic radiosurgery systems, comprised of two radio-opaque markers/fiducials 6 and 7 set at a fixed distance from one another housed in a rod shaped enclosure/fiducial housing 10. The fiducial housing 10 in this embodiment is made of durable aluminum, but in other embodiments may be made of other suitable and durable material known to one skilled in the relevant art. The fiducial housing 10 is attached to a rod 15 made of durable aluminum but in other embodiments may be made of other suitable and durable material known to one skilled in the relevant art. The rod 15 with the attached fiducial housing 10 is then assembled to the collimator fixture 20 which is equipped with a fastening mechanism 25 to keep the rod 15 firmly and securely in place. The fastening mechanism 25 operates with the same tightening action as a drill chuck or like device. The current design allows easy adjustment of rod 15 to reflect the different SAD setting.

Figure 2B:
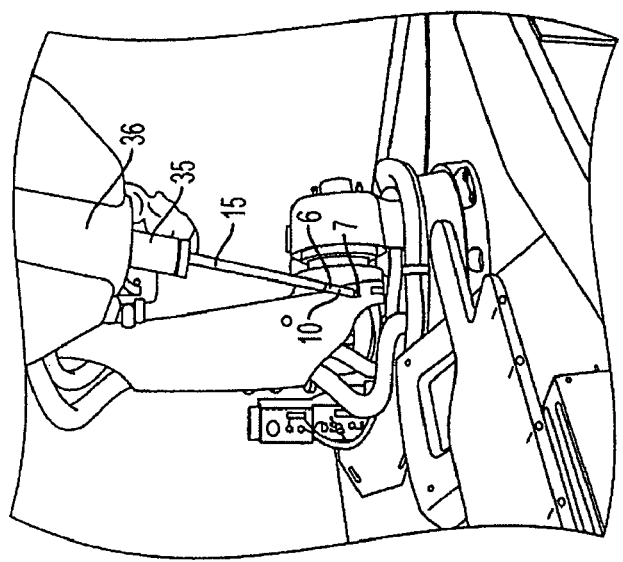
FIG. 2B is a diagram of the apparatus of the new invention as assembled and attached to the LINAC of a robotic radiosurgery system.
Figures 1, 2A:
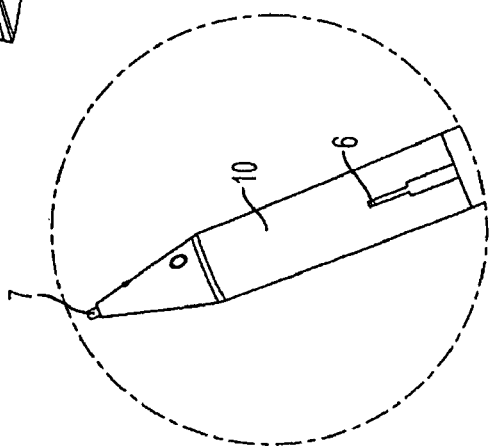
FIG. 2A is a drawing of the assembled apparatus of the new invention in its testing position and ready for attachment to the linear accelerator (LINAC) of a robotic radiosurgery system.
Figure 2A:
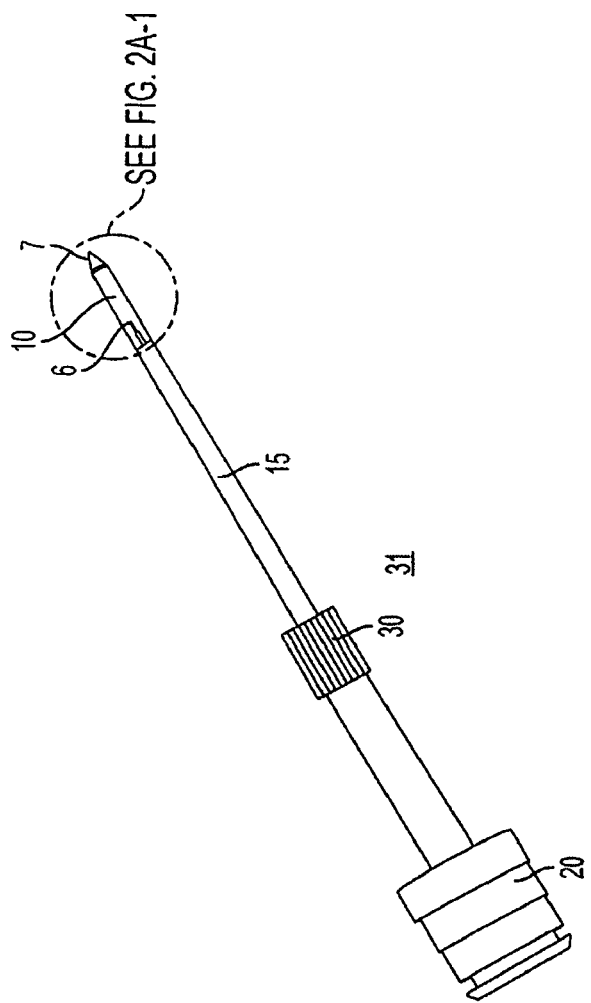

FIG. 2A is a diagram of the assembled apparatus 31 designed to access full beam geometry in image guided robotic radiosurgery systems in its testing position. The assembled apparatus is affixed to the linear accelerator (LINAC) 36 of a robotic radiosurgery system, as shown in FIG. 2B, via a collimator interface 35. The collimator interface 35 normally houses a collimater, but instead the collimator interface provides the point of attachment for the assembled apparatus 31 of the invention, where the collimator fixture 20 is securely inserted into the collimator interface 35. The two radio-opaque markers/fiducials 6 and 7 align with the beam central axis with mechanical precision of preferably better than 0.1 mm. In the current embodiment the length of the apparatus can be adjusted such that the distance from the radiation source to the radio-opaque marker/fiducial 7 at the distal end will be precisely known. FIG. 2A-1 is a superimposed view of the fiducial housing 10 highlighting the position of the radio-opaque markers/fiducials 6 and 7.

Figure 3:
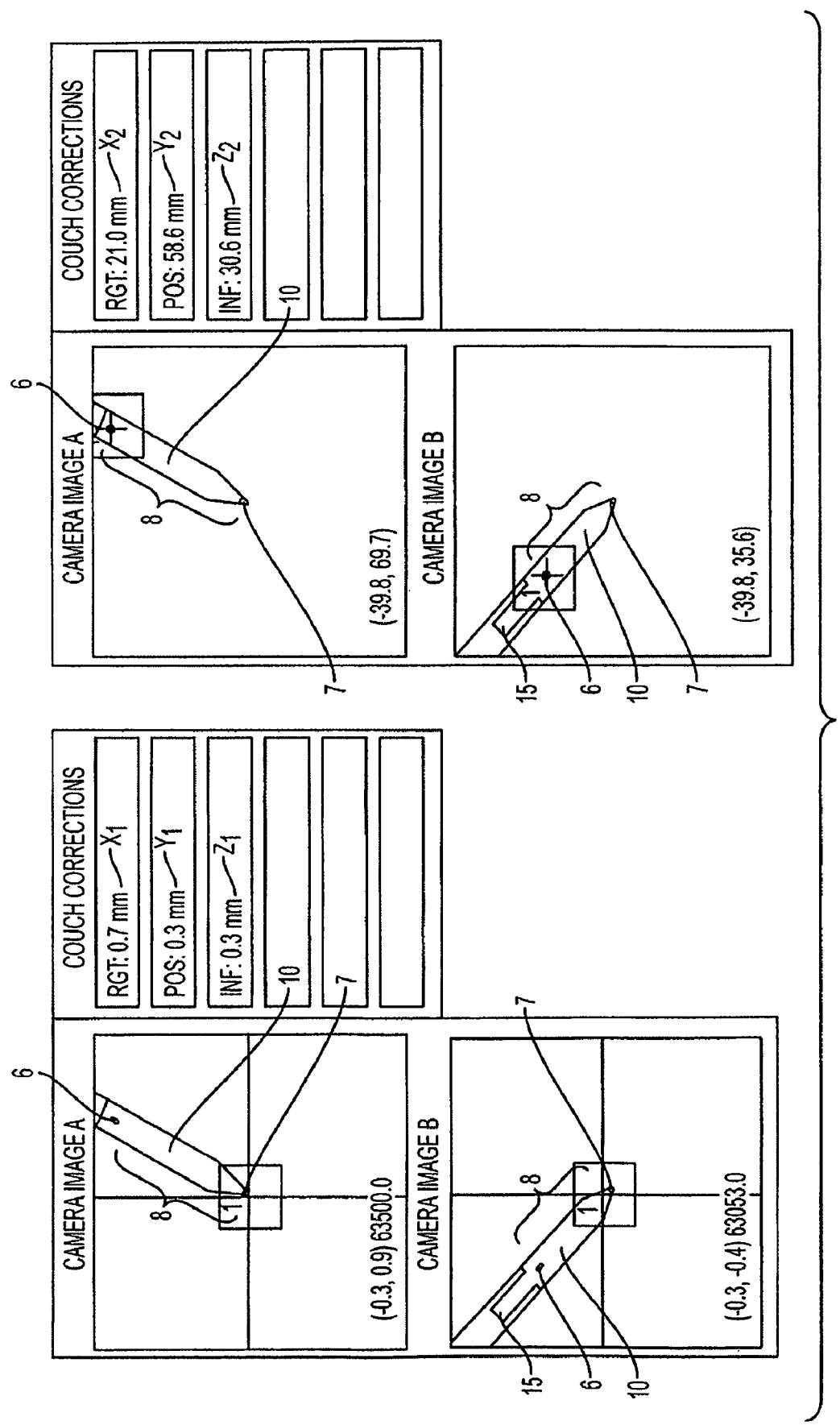
FIG. 3 is a diagram of the radiographic image pair produced by the new invention as captured by camera images.

A treatment plan is generated to position the LINAC 36 to a series of pre-defined radiation beam orientations (positions). A simulation of treatment is then carried out with the apparatus 31 attached to the LINAC 36 and images are taken at each LINAC 36 position as shown in FIG. 3. From the coordinates of the two radio-opaque markers 6 and 7 obtained from the radiographic images, the beam orientation can be derived by calculating its directional cosines using the following equations:

$$l = \cos \alpha = (x2-x1)/d, \ m = \cos \beta = (y2-y1)/d, \ n = \cos \gamma = (z2-z1)/d,$$

Where (x1, y1, z1) and (x2, y2, z2) are the coordinates of the two radio-opaque markers 7 and 6 respectively, and d is the distance 8 between the two radio-opaque markers 6 and 7.

Figure 4:
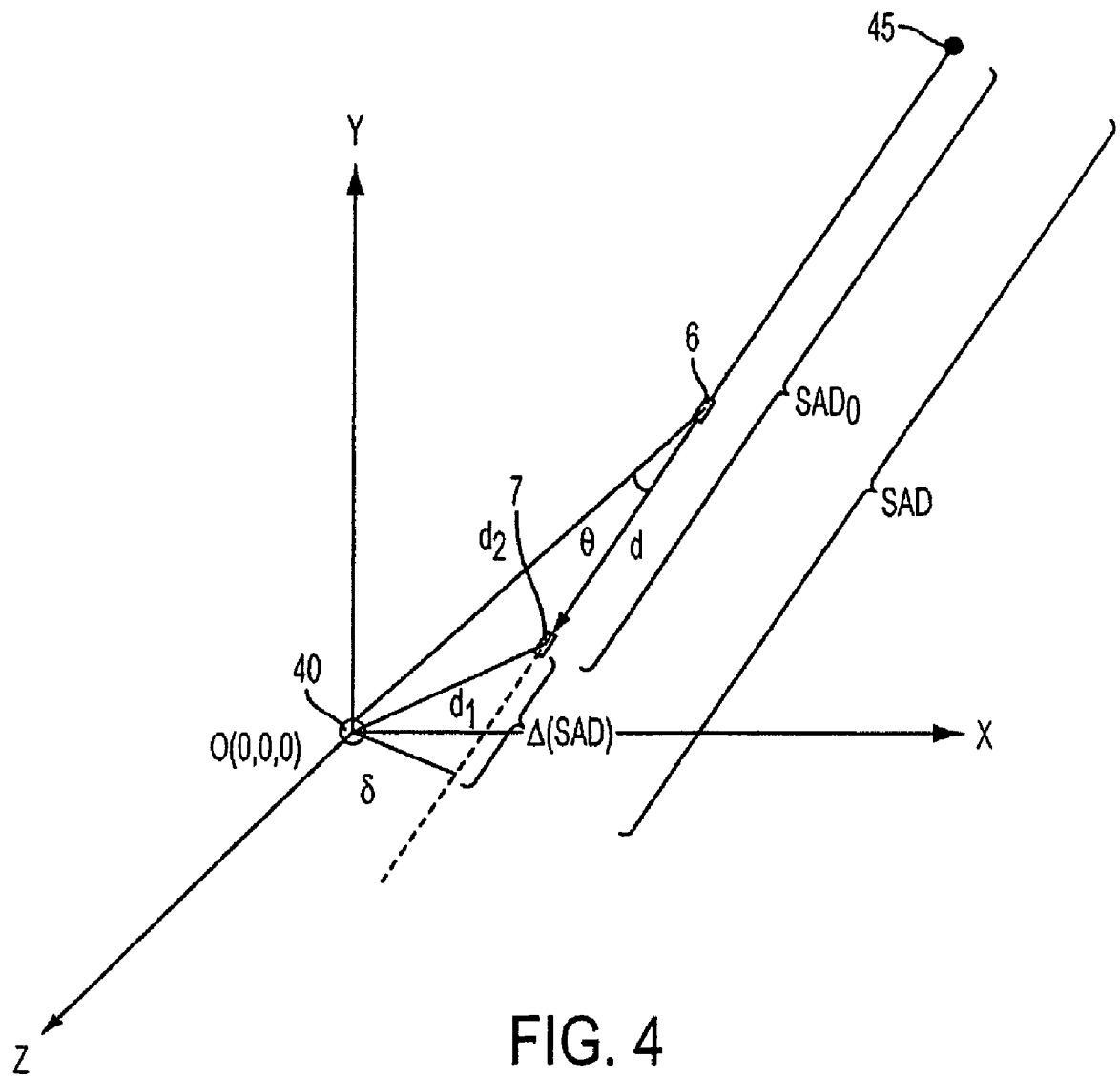
FIG. 4 is a graph illustrating the relevant geometric parameters of the new apparatus in relation to the coordinate system of a robotic radiosurgery system.

In FIG. 4, the graph illustrates that the distance between the system's origin 40 and marker one 7, is denoted as $d_1$, and that the distance between the origin 40 and marker two 6 is denoted as $d_2$. The beam off-axis error, $\delta$ can then be calculated using following equations:

$$\delta = d_2 \sin \theta,$$

where, $$\sin \theta = \sqrt{1 - \left(\frac{d^2 + d_2^2 - d_1^2}{2dd_2}\right)^2}$$

The actual radiation source 45 to iso-center distance (SAD) can be calculated as:

$$SAD = SAD_0 + \left(\frac{d^2 + d_2^2 - d_1^2}{2d} - d\right)$$

Where, $SAD_0$ is the distance between radiation source 45 and radio-opaque marker one 7 and the deviation in SAD is readily calculated using:

$$\Delta(SAD) = SAD - SAD_0 = \frac{d^2 + d_2^2 - d_1^2}{2d} - d$$

The results of above angular and distal calculation are then compared with the pre-defined beam position. The absolute deviations are derived for each test carried out with apparatus 31. The results from a set of periodic tests reflect the consistency or reproducibility of the beam orientations. If the imaging system is pre-calibrated, then the quantitative beam geometric information can be readily used to adjust the beam position settings.

The easily obtained results provide efficiency and accuracy of beam adjustment, reducing the time necessary for verifying beam geometry. Future embodiments of this invention will permit calculation of the beam geometric parameters with full automation. A more efficient and wider application of this present invention is envisioned when software is developed and integrated into robotic radiosurgery systems such as Cyberknife™.

It should be noted that the methods and apparatus described herein are not limited to use only with robotic radiosurgery treatment. In alternative embodiments, the methods and apparatus herein may be used in applications within other areas of the medical technology field as well as outside the medical technology field where "treatment" as used herein may refer generally to the application of radiation beams.

It is to be understood, that the subject invention described herein is not limited to the particular embodiments of the invention described herein, as variations of the particular embodiments may be made and still fall within the scope. It is also to be understood that the terminology employed is for the purpose of describing particular embodiments, and is not intended to be limiting.

The contents of all patents, patent applications, published articles, books, reference manuals and abstracts cited herein are hereby incorporated by reference in their entirety to more fully describe the state of art to which the invention pertains.

As various changes can be made in the above-described subject matter without departing from the scope and the spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

EQUIVALENTS

Those skilled in the art will recognize, or be able to ascertain using no more than routine experimentation, many equivalents to the specific embodiments of the invention described herein. Such equivalents are intended to be encompassed by the claims.

What is claimed is:

1. A method, comprising:
providing a LINAC with a radiation source having a beam central axis from which a treatment beam is emitted;

providing radio-opaque markers aligned within the LINAC's beam central axis, at a fixed distance from each other and at a predefined distance from the radiation source of the LINAC;

providing a housing for said radio-opaque markers that maintains their position relative to each other and the radiation source of the LINAC;

providing a means of attachment of the housing to the LINAC;

providing a radiographic image guidance system which is independent of the LINAC;

positioning the radio-opaque markers which are attached to the LINAC at a fixed distance from each other, and at a fixed distance from the LINAC's radiation source and aligned with the LINAC's beam central axis such that the radio-opaque markers' position in space give a physical representation of the beam central axis;

positioning the LINAC to a series of pre-defined positions;

generating stereotactic images of the radio-opaque markers at each pre-defined position using the radiographic image guided system which is independent of the LINAC;

analyzing the coordinates of the radio-opaque markers from the acquired images and calculating angular and distal parameters of each beam position to obtain beam geometry parameters where the coordinates of the radio-opaque markers are represented by values x1, y1, z1 and x2, y2, z2;

comparing and assessing the obtained beam geometry parameters with the values of the pre-defined beam positions.

2. The method of claim 1, wherein the calculation of beam geometry includes:

deriving a value of d, which is the distance between the radio-opaque markers, by an equation $d=\sqrt{[(x2-x1)^2+(y2-y1)^2+(z2-z1)^2]}$; and deriving directional cosines from equations $l=\cos\alpha=(x2-x1)/d$, $m=\cos\beta=(y2-y1)/d$, $n=\cos\gamma=(z2-z1)/d$.

3. The method of claim 2, wherein the calculation of the distal information of the radiation beam, includes:

deriving beam off-axis error using equation $\delta=d_2 \sin\theta$ where $d_2$ is the distance from the second marker to the system's origin and $\theta$ is the angle formed by the beam central axis and the line connecting the system's origin to the second radio-opaque marker;

deriving the radiation source iso-center distance (SAD) using the equation $$SAD = SAD_0 + \left(\frac{d^2 + d_2^2 - d_1^2}{2d} - d\right)$$

where $SAD_0$ is a pre-defined distance from the radiation source to the iso-center and $d_1$ is the distance from the first radio-opaque marker to the system's origin; and deriving the deviation of the SAD using the equation $$\Delta(SAD) = SAD - SAD_0 = \frac{d^2 + d_2^2 - d_1^2}{2d} - d.$$

4. The method of claim 3, wherein the angular and distal information derived is used to determine the difference between the actual and pre-defined beam position.

5. An apparatus for obtaining beam geometry comprising:

two or more radio-opaque markers set at a fixed distance from each other and at a pre-defined distance from a radiation source of a LINAC and aligned with the LINAC's beam central axis;

a housing for said radio-opaque markers that maintains their position relative to each other and the radiation source of the LINAC;

a means or device for attachment of the housing for the radio-opaque markers to the LINAC such that the radio-opaque markers remain positioned at a pre-defined distance from the radiation source, and aligned with the LINAC's beam central axis;

the apparatus maintains the relative position of the radio-opaque markers to the LINAC's radiation source and the LINAC's beam central axis for different beam positions; and the apparatus at each beam position is imaged using a radiographic system which is independent of the LINAC and the location of the radio-opaque markers in the image is used to determine the deviation and error in the actual and pre-defined beam positions.

* * * * *